United States Patent [19]

Irikura et al.

[11] 3,937,821

[45] Feb. 10, 1976

[54] PLASMA SUBSTITUTE INCLUDING ARTIFICIAL STARCH AND METHOD FOR THE PREPARATION THEREOF

[75] Inventors: Tsutomu Irikura, Tokyo; Kazunari Shirai, Tokyo; Mamoru Tada, Urawa; Terumi Tamada, Tokyo; Jun Imai, Ageo, all of Japan

[73] Assignee: Kyorin Seiyaku Kabushiki Kaisha, Japan

[22] Filed: Nov. 19, 1973

[21] Appl. No.: 416,725

Related U.S. Application Data

[63] Continuation of Ser. No. 213,553, Dec. 29, 1971.

[30] Foreign Application Priority Data

Aug. 21, 1971 Japan.............................. 46-63838

[52] U.S. Cl............................. 424/180; 260/209 R
[51] Int. Cl.$^2$........................................... A01N 9/28
[58] Field of Search..................................... 424/180

[56] References Cited
OTHER PUBLICATIONS

*Dispensatory of the United States of America*, 25th ed., published by J.B. Lippincott Co., Phila., 1955, pp. 1194–1195.

*Dispensatory of the United States of America*, 25th ed., published by J.B. Lippincott Co., Phila., 1955, pp. 1196–1197.
Tamada et al., *Chem. Pharm. Bull.*, Vol. 19, pp. 286–291, Feb. 1971.

*Primary Examiner*—Lewis Gotts
*Assistant Examiner*—Cary Owens
*Attorney, Agent, or Firm*—Toren, McGeady and Stanger

[57] ABSTRACT

A process for preparing a pyrogen-free plasma substitute consisting of treating hydroxyethyl starch having a DS of 0.5 – 0.6 (preferably 0.55) and an intrinsic viscosity of 0.28 – 0.30 with an acid to lower the molecular weight; adjusting it to the desired hydroxyethyl starch having a DS of 0.55 and an intrinsic viscosity of 0.08– 0.14; adding a depyrogen reagent, such as Raney-nickel to it, if necessary, obtaining an isotonic aqueous solution containing 6% of hydroxyethyl starch and other various salts, preferably, adding sodium chloride (0.5%), potassium chloride (0.03%), calcium chloride dihydrate (0.02%), sodium lactate (0.224%), and glucose (1%)(W/V%) to 6% hydroxyethyl starch solution; and then adjusting the pH of the obtained iostonic aqueous solution to 6.2 ± 0.5.

5 Claims, 12 Drawing Figures

Fig. 1 Blood Polysaccharides Concentrations after Infusion of HES, Soluble Starch, Dextran and PVP into Rabbits.

Fig.2 Relations between DS of HES and Blood Polysaccharides Concentration or Excretory Rate in Urine after Infusion into Rabbits o———o Blood polysaccharides 3 hours after the infusion
●———● 6 hours
⊙———⊙ 24 hours
✕---✕ Excreted polysaccharides in urine for 24 hours Fig. 3 Relation between Average Molecular Weight and Intrinsic Viscosity Fig. 4 Relation between Half Life and the Intrinsic Viscosity of Hydrolysates of HES Half life was a time from the end of infusion of hydrolysates of HES, enough for the disappearance of 50% blood polysaccharides.

Fig. 5 Relation between DS and Hydrolysis Rate by pig pancreas α-amylase in vitro

Incubation was performed in 0.02M phosphate buffer, pH 6.9, at 30°C. Concentration of substrate and enzyme were 10mg/ml and 0.5µg/ml, respectively.

a) Hydrolysis rate was expressed in terms of $10^2$ mg of maltose liberated per unit enzyme in one minute ($10^2$ mg/min/unit).

Fig. 6 Influence of plasma expanders on the red blood cells of rabbit after 60 minutes of incubation

Physiological salt solution

HES ex.7 preparation

Dextran (75,000) preparation

Dextran (45,000) preparation

Artificial gelatin preparation (plasmagel)

Fig. 7 Influence of plasma expanders on the human red blood cells after 60 minutes of incubation

Physiological salt solution

HES ex. 7 preparation

Dextran (75,000) preparation

Dextran (45,000) preparation

Artificial gelatin preparation (gelofusine)

Artificial gelatin preparation (plasmagel)

Fig. 8 Effect on Arterial Blood pressure of Dog

Fig. 9. Effect on pH of Arterial Blood in Dog

Fig.10  Blood and Urinary Concentration of HES in Rabbits following Infusion 30ml/kg of HESPANDER.

The concentration was plotted as % to the concentration at the end of infusion. Blood concentration of dextrans (molecular weight 75,000 and 40,000) were expressed respectively for comparison.

●————● HES in urine     △--------△ Dextran-75 in blood
○————○ HES in blood     ▲--------▲ Dextran-40 in blood
        (HES;DS 0.55, η 0.10)

Fig.11 Liver and Kidney from Rabbit 10 days after 100ml/Kg transfusion of plasma expander HES preparation(ex.7)

Dextran(75,000)preparation

Liver; PAS stain          Kidney; HE stain

Fig.12 Gel-filtration on Sephadex G-200 of Native HES (DS 0.55, η 0.30) and HES preparation (DS 0.55, η 0.10)

PLASMA SUBSTITUTE INCLUDING ARTIFICIAL STARCH AND METHOD FOR THE PREPARATION THEREOF

This is a Continuation of Application Ser. No. 213,553, filed Dec. 29, 1971.

This invention relates to an excellent plasma substitute including artificial starch which is able to be used with safety and effectiveness for clinical use. The new plasma substitute relating to this invention is very useful for maintaining blood pressure in the case of hemorrhogic shock without provoking the adverse reactions such as the accumulation of colloidal substances in tissue and destruction, and agglutination of red cell as is frequently observed by using polymers as a plasma substitute. Moreover, the present plasma substitute in this invention has an excellent character that it can be administrated intravenously in large amounts without chill, fever and antigenicity because the procedure of depyrogen is carried out in the technical processes for production of the injection. To date, many kinds of colloidal plasma expanders and substitutes have been applied to clinical use. Although most of the colloidal substances are not homogeneous substances physiologically, such colloidal substances having a high viscosity possess an increased capacity for maintaining the blood pressure. On the other hand, the lack of excretion of such substances into the urine is so insufficient that tissue lesions due to its accumulation are apt to occur. Such colloidal substances include Arginine, Gelatin, and Polyvinylpyrrolidone (PVP), etc. In the present time, it is clinically preferable to use Dextran or artificial gelatin. However, there are defects in the Dextran, or artificial gelatin, too. That is to say, Dextran causes renal lesion or anaphylactic shock to 6 – 8 percent of the patients to whom it is given. Owing to the gelification of artificial gelatin at room temperature, it is unhandy to use in the case of an emergency. Moreover, the artificial gelatin causes the destruction of red cells. It is difficult to say that both Dextran and artificial gelatin are ideal raw materials for plasma expanders and substitutes. Generally speaking, starch, of which the structure is similar to glycogen, is acceptable to the body tissues because the starch does not function as a foreign substance in vivo. In particular, soluble starch is hydrolyzed so rapidly by α-amylase in the blood that it can't be used as plasma substitute.

Since Wiedersheim reported in 1957 that a hydroxyethylated starch was available as a plasma substitute because of its weak toxicity and strong resistivity to α-amylase, the researches into hydroxyethyl starch (abbreviated as HES hereinafter) for use as a plasma expander have been continued by numerous investigators. But the attention of the investigators had been directed to an effect only for maintaining blood pressure by way of using hydroxyethyl starch having a high DS (degree of substitution of hydroxyethyl group) and high molecular weight. As a result of this fact, the excretion, accumulation, and hydrolysis of HES in body tissue have been ignored. The present inventors traced that the reason why it was impossible to use the colloidal solution as the plasma substitute was due to its causing tissue lesions from to the accumulation of the substances administrated as plasma substitute. As a result, the very important point on the research is directed to the fact that a tissue lesion is not caused by the administration of HES, even if the plasma expanding effect decreases slightly.

The present invention is accomplished based on the following items.

1. The concentration of the ccolloidal substances in blood and urine after intravenous infusion of HES, soluble starch, Dextran, and PVP into rabbits.

Figure 1:
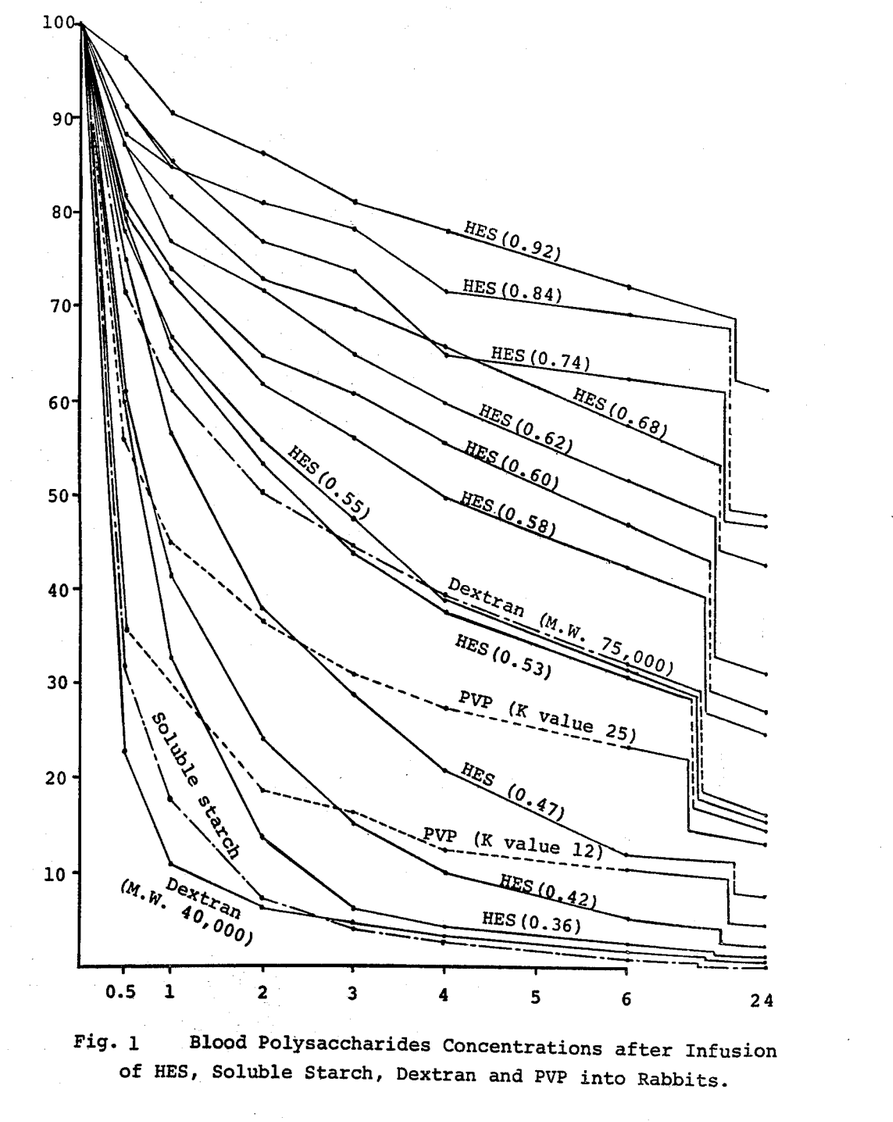
FIG. 1 shows blood polysaccharides concentrations after infusion of HES, Soluble Starch, Dextran and PVP into Rabbits.
Figure 2:
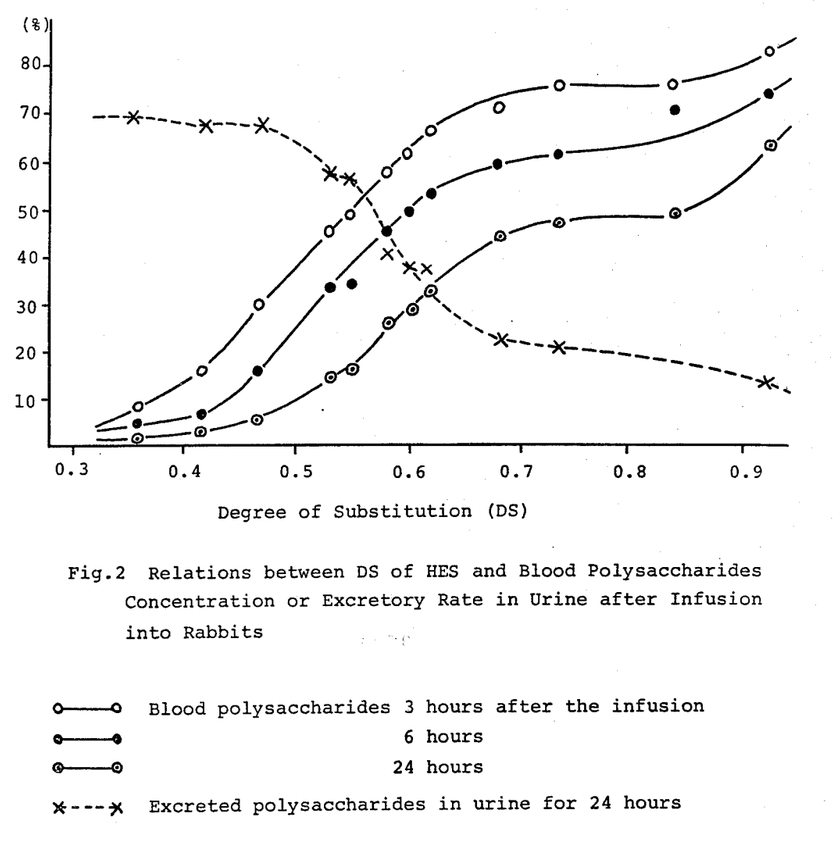
FIG. 2 shows relations betwees DS of HES and blood polysaccharides concentration of Excretory Rate in Urine after infusion into Rabbits.

After administrating intravenously the isotonic solutions containing 6% of HES with various DS, Dextran commercial available, 6% of soluble starch, and 3.5% and 6% of PVP, the concentrations of colloidal substances in blood are measured each hour. As shown in FIG. 1, in proportion to the increase of molecular weight, HES disappears slowly from blood and HES with high DS is more persistent in the blood when the HES is equal in molecular weight. Furthermore, the relation between the persistence of the colloidal substances in blood and the excretion into urine is shown in FIG. 2. From FIGS. 1 and 2, the persistence of HES with DS 0.5 – 0.6 in blood is nearly equal to that of Dextran (average molecular weight 75,000). Therefore, it is concluded that HES with DS 0.55 was preferable to use as plasma substitute.

2. The relation between the molecular weight and intrinsic viscosity of HES and its half-life period in blood.

Pathological examinations for main tissue are carried out by the intravenous infusion of HES (DS 0.54 and molecular weight 233,600) which shows the same concentration in the blood as Dextran (average molecular weight 75,000) and Dextran into rabbits daily for one month. The lesion of the main tissue is not observed in 10 and 30 ml/kg treated rabbits but a stronger lesion is observed in 90 ml/kg of HES treated rabbits than in Dextran treated rabbits. From consideration of the above results, after hydrolyzing HES with hydrochloric acid to prepare the desired HES with a low molecular weight, the relation between the molecular weight and intrinsic viscosity, and a half-life period in blood of hydrolysed HES are obtained.

Figure 3:
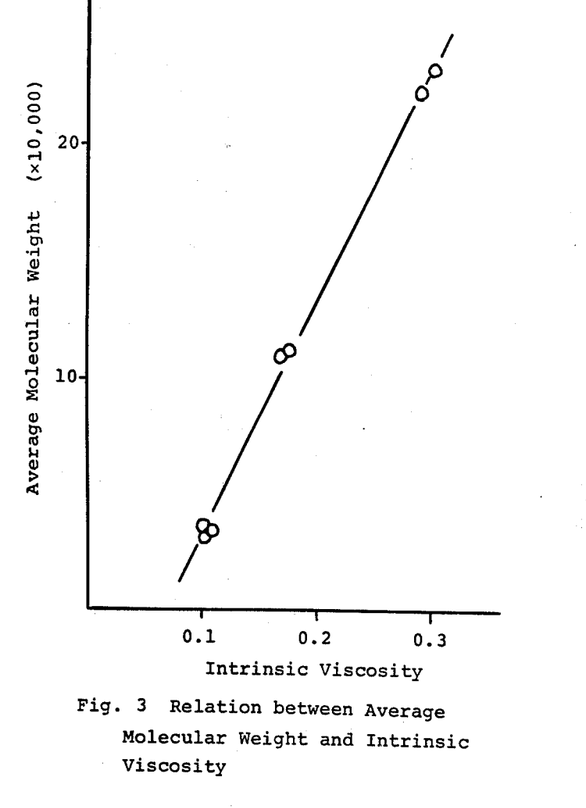
FIG. 3 shows relation between average molecular weight and intrinsic viscosity.

FIG. 3 shows the relation between the intrinsic viscosity and molecular weight which is determined by Archibald's method. The following equation is established from FIG. 3.

Figure 4:
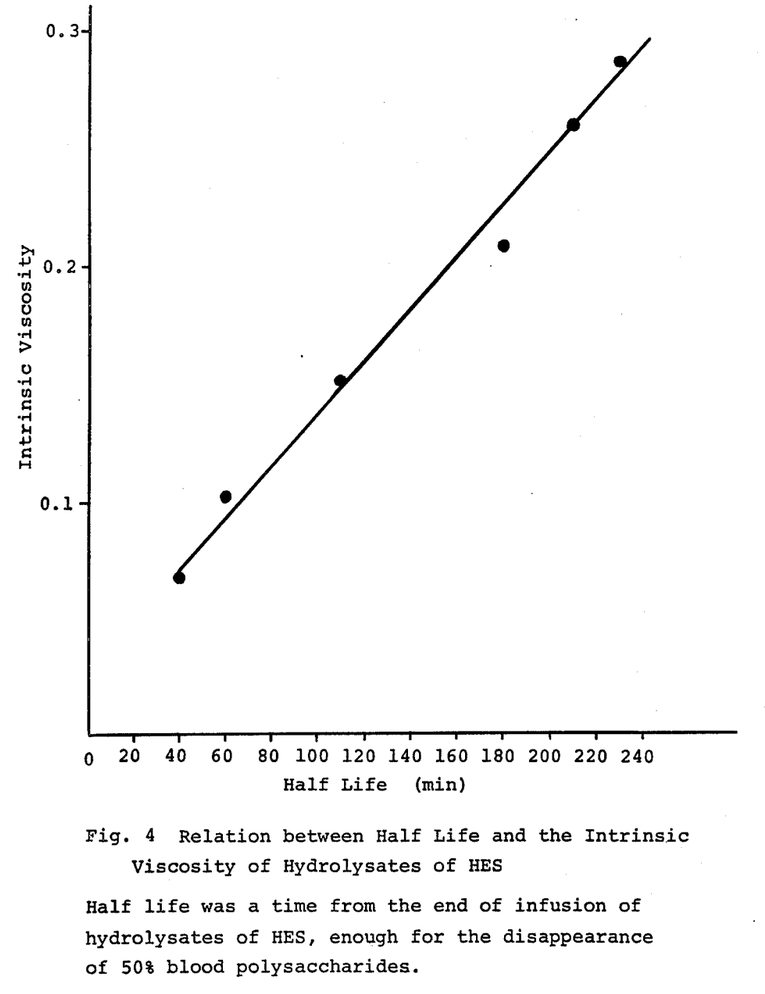
FIG. 4 shows relation between half life and intrinsic viscosity of hydrolysates of HES.

Average Molecular Weight = $1.037 \times 10^6 \times [\eta] - 7.360 \times 10^4 [\eta] : 0.103 - 0.300$ Next, FIG. 4 shows the relation between the intrinsic viscosity and a half-life period (min.) of HES with DS 0.5 – 0.6 in blood. From the relation obtained above, the intrinsic viscosity of HES may be considered as an objective and reliable indication of the quality of HES; therefore it is possible to select the HES having the high safety based on the intrinsic viscosity.

3. Hydrolysis rate of HES by pig-pancreas α-amylase

Figure 5:
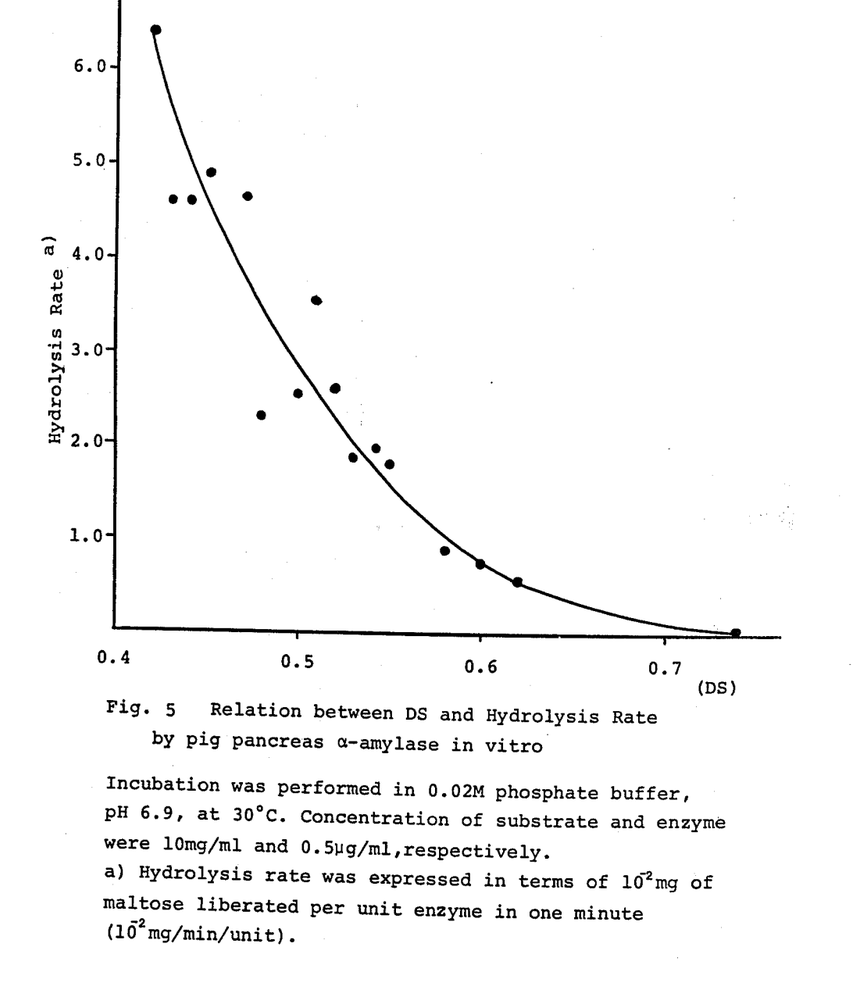
FIG. 5 shows relation between DS and hydrolysis rate by pig pancreas α-amylase in vitro.

The hydrolysis rate of HES by α-amylase is dependent only on the degree of substitution of the hydroxyethyl group without considering the molecular weight of HES. In the case of a condition wherein 77% of the soluble starch is hydrolyzed by α-amylase, HES with a DS of 0.92 is not decomposed. FIG. 5 shows the resistance against α-amylase of HES in the range of DS 0.4–0.7. From FIG. 5, it may be considered that HES with a high DS remains in the body tissue for a long period because the HES with more than DS 0.6 is resistant to α-amylase and is less subject to hydrolysis. According to 1 - 3 mentioned above, HES with DS 0.5–0.6 and an intrinsic viscosity of 0.08–0.14 is preferable to use as a plasma substitute. However, there are indicated factors which must be clarified to produce the HES preparation in a commercial scale. That is to say, it is required for the HES preparation that the molecular weight of the HES with a molecular weight 200,000–300,000 as raw material must be constantly reduced to the desired molecular weight and that the turbidity caused by colloidal substances and pyrogen must be completely removed.

Fortunately, it is clarified that it may be able to obtain the desired HES with constant low molecular weight by treating the high molecular HES in dilute solution with a dilute acid and also to remove the white turbidity by its treatment, as shown in the examples. Additionally, if the HES is contaminated with pyrogen, it can be easily removed using the technique in the Japanese Pat. No. 609,559 by the present inventor. By these treatments, the technical problems have now been resolved. Further, in order to obtain the ideal plasma substitute for clinical use, all of the examinations such as the safety to the red cells, the ability for maintaining the blood pressure, the prevention of acidosis, and the rapid disappearance from the tissues in the case of intravenous infusion in large amounts are carried out, respectively. As the results of the following examinations (4–9), it is confirmed that the HES preparation as shown in the Example 7 is most appropriate.

4. Lowering of the acute toxicity.

HES preparation (Example 7) is compared with 6% HES (DS 0.54, η 0.300) which is not treated with acid and Dextran (M.W. 75,000). From the results, it can be stated that the safety of the HES preparation increases exceedingly according to the lowering of its acute toxicity as shown in Table 1.

5. Morphological influence on red cells.

Figure 6:
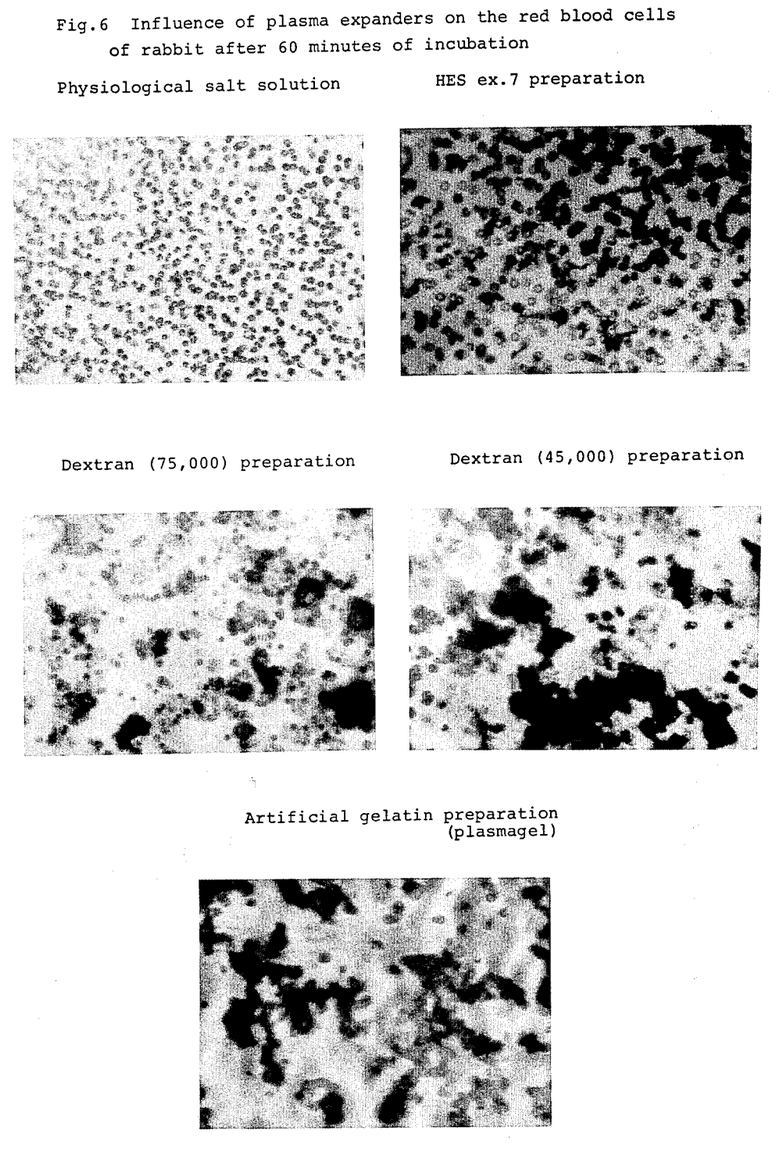
FIG. 6 shows influence of plasma expanders on the red blood cells of rabbit after 60 minutes of incubation.
Figure 7:
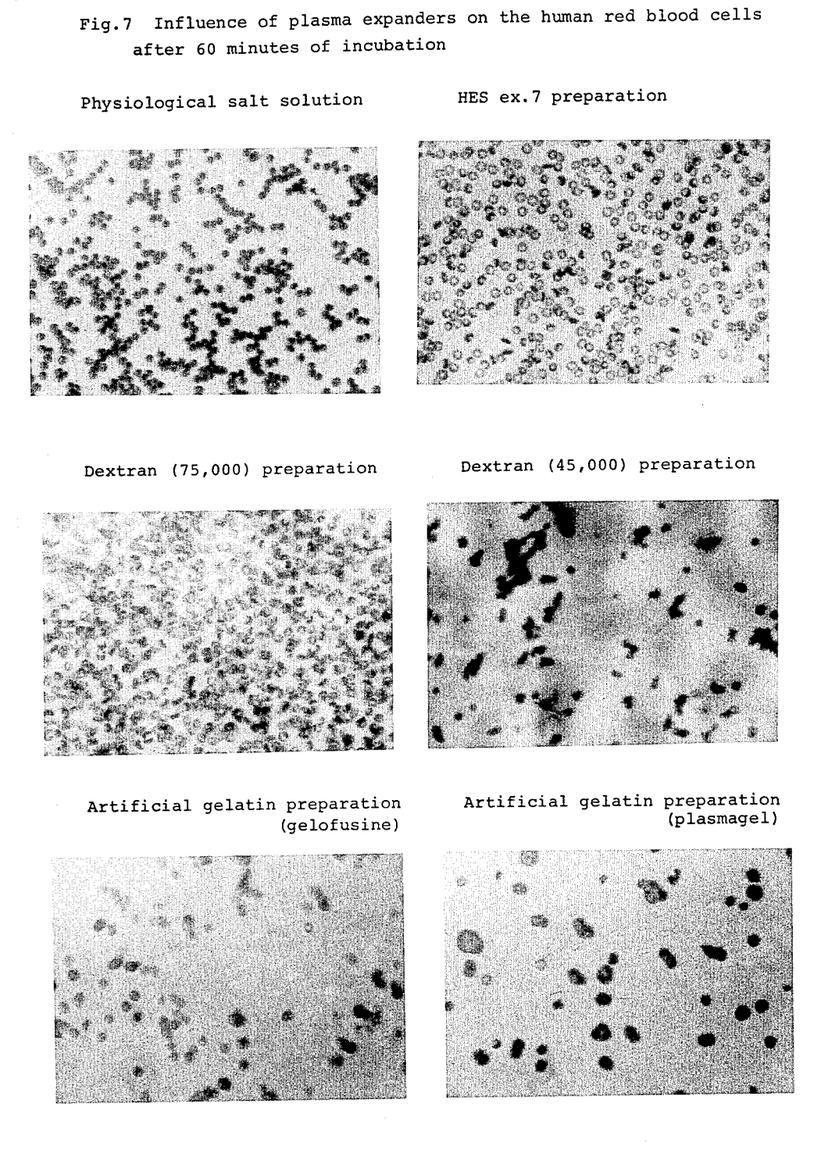
FIG. 7 shows influence of plasma extenders on the human red blood cells after 60 minutes of incubation.

Isotonicities of various plasma substitutes are examined by morphological change of red cells after rabbit and human red cells are incubated with plasma substitute. In the case of saline and the HES preparation (Example 7), the morphological change of red cells is not observed, respectively. Red cells of rabbit incubated with low molecular weight Dextran (M.W. 40,000) and clinical Dextran (M.W. 70,000) are agglutinative. Some artificial gelatin preparations show the worst influence for red cells as shown in FIGS. 6 and 7.

Table 1

| | | | $LD_{50}$ Values (ml/kg) of HES (DS 0.55 & M.W. 230,000) and HESPANDER | | |
|---|---|---|---|---|---|
| Animals | route | sex | ex.7 preparation | HES (DS 0.55 & M.W. 230,000) 6% in Saline | Dextran-75 |
| Rabbits | i.v. | male | 416 | 225 | — |
| | | female | 419 | 230 | 323 |
| Mice | i.v. | male | 360 | 210 | 208 |
| | | female | — | 216 | 202 |
| | i.p. | male | >600 | >450 | — |
| | | female | >600 | >450 | — |
| Rats | i.v. | male | 262 | — | 136 |
| | | female | 193 | — | 125 |

6. The effect for maintaining blood pressure in a hemorrhagic dog

Figure 8:
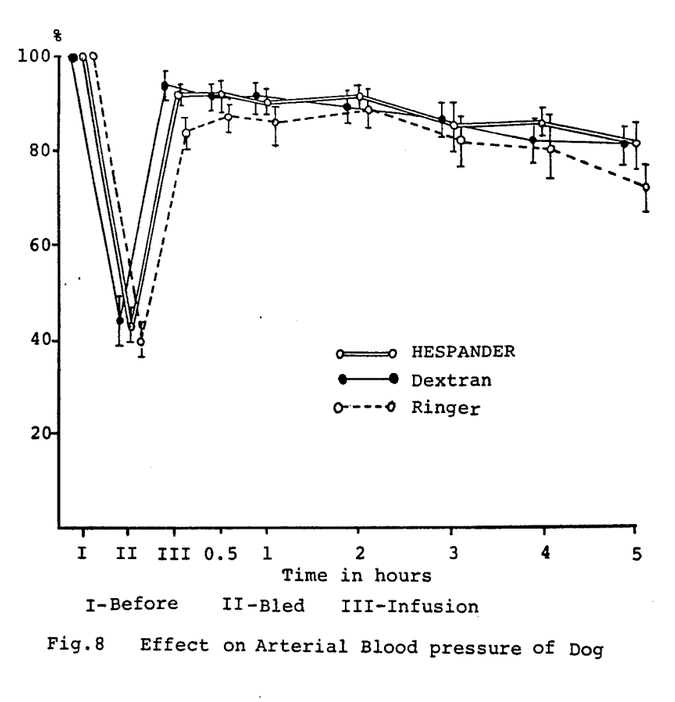
FIG. 8 shows effect on arterial blood pressure of Dog.
Figure 9:
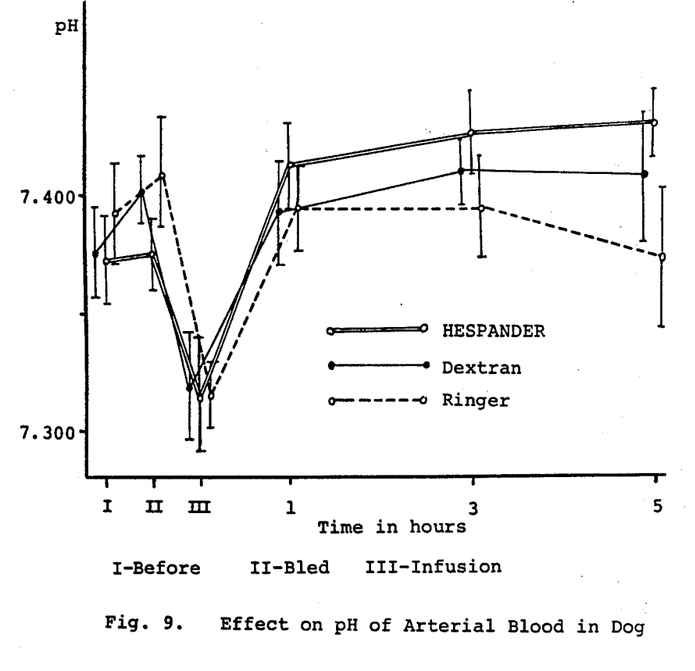
FIG. 9 shows effect on pH of arterial blood in Dog.

When anesthetized dogs are bled the volume of 30 ml/kg at the bleeding rate of 10 ml/min. and immediately receive an equal volume of the plasma substitute (6% HES in 0.9% NaCl) by an intravaneous adminstration, the plasma substitute shows the same effect for maintaining arterial blood pressure of the treated dogs as Dextran (average molecular weight 75,000) as shown in FIG. 8. The pH value of arterial blood of a Ringer treated dog changes to acidic as shown in FIG. 9. On the other hand, the HES preparation (Example 7) can prevent a tendency to acidosis of arterial blood.

7. Persistence of HES in blood of rabbit

Figure 10:
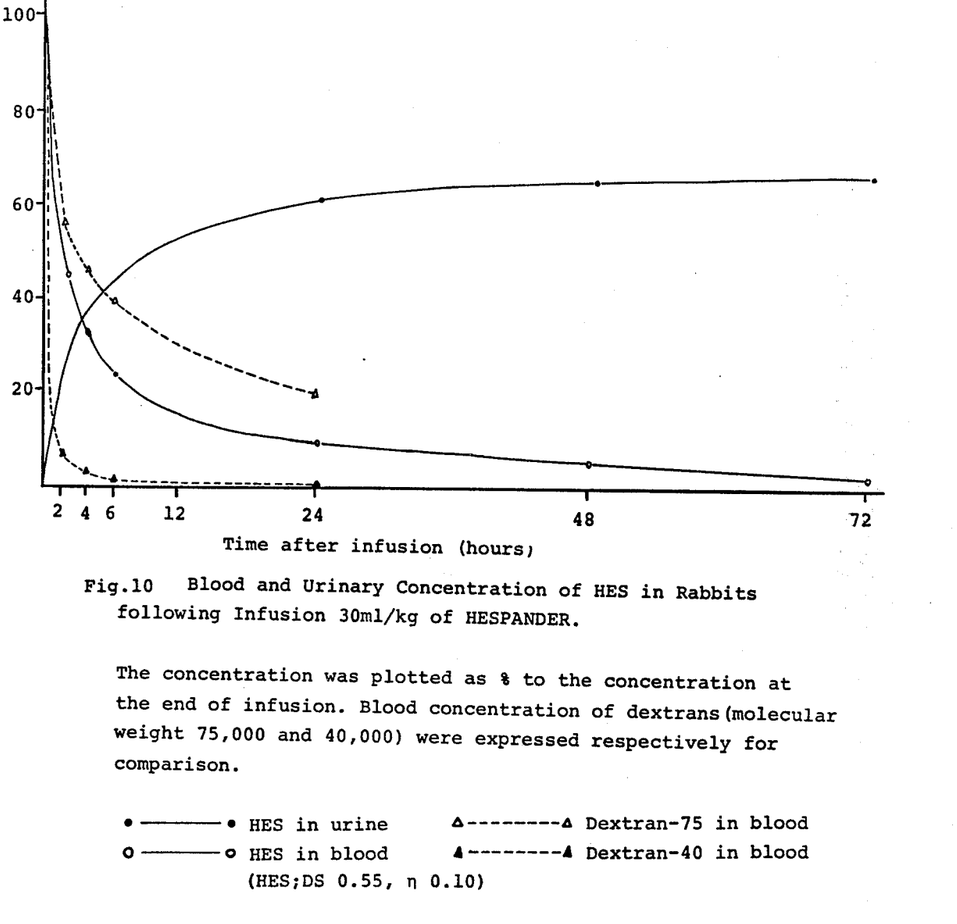
FIG. 10 shows blood and urinary concentration of HES in Rabbits following infusion 30 ml./kg of Hespander.

The concentration of colloidal substances which remain in blood is examined after intravenous infusion into a rabbit. The rate of disappearance of HES (Example 7) in blood is slightly rapid as compared with clinical Dextran, but the persistence of HES in the blood is enough to manifest the activity as a plasma substitute as compared with Dextran (average molecular weight 40,000) (see FIG. 10).

8. Examination on accumulation of HES

Figure 11:
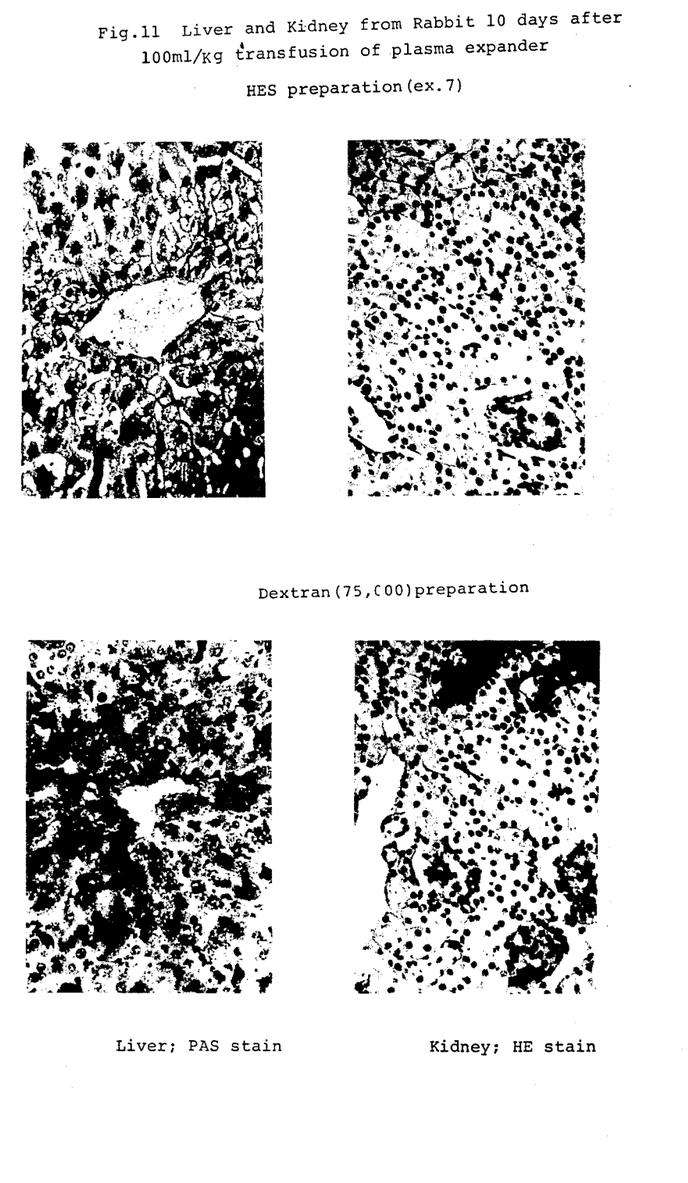
FIG. 11 shows liver and kidney from Rabbit 10 days after 100 ml./kg transfusion of plasma expander.

The accumulation of HES (Example 7) in tissues is not observed in the case of the usual dose after intravenous infusion of it into mouse. Additionally, even if the presence of HES is observed instantly in liver and spleen, the functional lesion of the reticuloendo therial system is not caused. When clinical Dextran (average molecular weight 75,000) is infused intravenously into rabbit in large amounts (100 ml/kg) at a time, the histological lesions of kidney and liver are observed. On the other hand, no lesion of the kidney and liver is observed by administrating intravenously the same amount of HES (Example 7). FIG. 11 shows photographs of tissues of corresponding kidney and liver.

9. Anaphylactoid reaction

The anaphylactoid reaction of rate and mice to Dextran has been known as consisting of edema and erythema of paws, ears and snout. In addition the occurrence of a combined anaphylactoid and purpuric reaction, when an injection of agar is given prior to Dextran, has been demonstrated. Investigators emphasize the role of histamine release from mast cells.

The present experiment is aimed at clarifying the possibility of the occurrence of anaphylactoid reaction in rats and mice injected with HES preparation (Example 7) and agar.

An intravenous injection of Dextran produced an acute, serous anaphylactoid inflammation in the ears, snout and tail of rats and mice. On the other hand, in animals injected with Example 7 preparation, no such inflammation was observed. Moreover anaphylactoid purpura appeared in the paws, ears and tail of rats and mice when an injection of agar was given prior to Dextran. In animals injected with the Example 7 preparation and agar, no symptoms of anaphylactoid purpura were obtained. These results suggest that the Example 7 preparation do not release histamine from mast cells under the conditions employed.

Immunogenicity

Rabbits, guinea pigs and mice received injections of Dextran or Example 7 preparation with complete Freud's adjuvant. Sera from all bleedings were analysed by passive cutaneous anaphylaxis reaction. Arthus reaction in rabbits and active anaphylaxis reaction in guinea pigs were performed too.

No antibodies to Dextran and the Example 7 preparation were detectable in rabbits and guinea pigs. This indicates that, under the conditions of immunization and testing employed, Dextran and the Example 7 preparation are not immunogenic in rabbits and guinea pigs.

When mice were injected with small quantities of Dextran or the Example 7 preparation, circulating antibodies were detected. But mice could be paralysed by the injection of relatively large quantities of polysaccharides. Large volumes of Dextran or Example 7 preparation, given via the intravenous route to nonimmunized humans do not lead to antibody production. Perhaps such large doses in man induce a state of immunological paralysis as in mice.

It has been shown that human sera contain Dextran reacting antibodies of varying types. These antibodies react with Dextran after infusion, so anaphylactic reaction occurs.

One hundred and six normal human sera were investigated by passive cutaneous anaphylaxis reaction in the pressence of antibodies reacting to Dextran or the Example 7 preparation. Three sera gave positive a reaction to Dextran. One of them reacted weakly to the Example 7 preparation. As described above, it is suggested that the Example 7 preparation possesses less possibility of the occurrence of anaphylactic reaction than Dextran.

EXAMPLE 1

Twenty eight gr. of hydroxyethylstarch (DS 0.50 to 0.60, intrinsic viscosity 0.28 to 0.30) were dissolved in 80 ml of distilled water for injection (Japanese Pharmacopoeia VIII) at about 50°C under stirring. To the resultant solution, 35 ml of 0.5 N—HCl and 0.1–1.0 gr. of activated charcoal were added and the mixture was gently boiled for 1 hour. After cooling, either 1N—NaHCO$_3$ or 1N—NaOH was added to adjust the pH to 7.0–7.4. When the reaction mixture was not pyrogen-free, it was treated with 5–50mg of depyrogen reagent (preferably, Raney nickel).

The insoluble material was removed by filtration, and the obtained solution was filtered clearly.

The filtrate was adjusted to 400 ml in total volume with distilled water for injection (Japanese Pharmacopoeia VIII). The resultant solution was a viscous and clear aqueous solution which contained 5.8–6.2% of hydroxyethylstarch and sodium chloride, and showed a turbidity of 6.1 ppm and viscosity of 1.85 cp (intrinsic viscosity 0.08 – 0.14). The isotonic injection for plasma substitute was obtained by adding moderately NaCl and another salts to this solution.

EXAMPLE 2

Seven gr. of hydroxyethylstarch (DS 0.5–0.6, intrinsic viscosity 0.30) were dissolved in 80 ml of distilled water for injection (Japanese Pharmacopoeia VIII) at about 50°C under stirring.

To this solution, 1.0 ml of 1N—HCl and 0.1–1.0 gr. of activated charcoal were added and the mixture was gently boiled for 1 hr.

After cooling, 1N—NaHCO$_3$ or 1N—NaOH was added to adjust the pH to 7.0–7.4.

When the reaction mixture was not pyrogen-free, it was treated with 5 – 50 mg of depyrogen reagent (preferable, Raney Nickel). The mixture was filtered to obtain a clear solution, and then the filtrate was adjusted to 100 ml in total volume with distilled water for injection (Japanese pharmacopoeia VIII). Moreover, NaCl, KCl, CaCl$_2$, Na-lactate and glucose were moderately added to this solution.

As a result, the isotonic injection for plasma substitute was obtained.

EXAMPLE 3

Fourteen gr. of hydroxyethylstarch (DS 0.5–0.6, intrinsic viscosity 0.30) were dissolved in 140 ml of distilled water for injection (Japanese Pharmacopoeia VIII) at about 50°C under stirring.

To the resultant solution, 3.26 ml of 0.5N—HCl and 0.1–1.0g of activated charcoal were added and the mixture was gently boiled for 1 hour.

After cooling, 1N-NaHCO$_3$ or 1N-NaOH was added to adjust the pH to 7.0–7.4. When the reaction mixture was not pyrogen-free, it was treated with 1–50mg of a depyrogen reagent such as Raney Nickel. This mixture was filtered to obtain a clear solution, and then the filtrate was adjusted to 200 ml of isotonic solution in total volume by adding distilled water for injection (Japanese Pharmacopoia VIII), NaCl, KCl, CaCl$_2$, Na-lactate and glucose.

The resultant solution was capable for to use as a product by means of packing, sealing and sterilizing by heating at 100°C for 1 hour.

EXAMPLE 4

Fourteen gr. of hydroxyethylstarch (DS 0.5–0.6, instrinsic viscosity 0.30) were dissolved in 140 ml of distilled water for injection (Japanese Pharmacopoeia VIII) at about 50°C under stirring.

To this solution, 3.26 ml of 0.5N-HCl was added and it was kept at 100°C for 1 hour and cooled. If necessary, the mixture was treated with activated charcoal. After cooling, the mixture was adjusted to a pH of 7.0–7.4 with 1N—NaHCO$_3$ or 1N—NaOH, and then 1.0g of NaCl, 0.06g of KCl, 0.04g of CaCl$_2$.2H$_2$O, 0.448g of Na-lactate and 2g of glucose were added and dissolved in this solution. If necessary, a depyrogen reagent such as 1–50mg of Raney nickel was added and heated at 90°–100°C for 30 minutes, and then activated charcoal was subsequently added, completely stirred and filtered.

The resultant solution was adjusted to 200 ml in total volume with distilled water for injection (Japanese Pharmacopoeia VIII) and pH was adjusted to 6.2 ± 0.5. The solution was filtered clearly, packed in a container and sealed.

It was used as a product through sterilizing by heating at 100°C for 1 hour.

EXAMPLE 5

When hydroxyethylstarch was hydrolyzed by HCl with the same manner as Example 1, the HES solution exhibted the values of turbidity (ppm) and viscosity (cp) depending on the concentration of HCl as shown in Table II.

Table II

| Relations between HCl-concentration and turbidity or viscosity of HES | | |
|---|---|---|
| HCl-concentration (normal) | turbidity (ppm) | viscosity (cp) |
| 0.00625 | 22.6 | 4.64 |
| 0.01250 | 18.0 | 3.11 |
| 0.01875 | 10.5 | 2.34 |
| 0.02500 | 8.0 | 1.87 |
| 0.03125 | 4.0 | 1.57 |
| 0.03750 | 4.3 | 1.57 |

(1) The turbidity was measured by nephlometer (TY3 Type; Made in Corp. Elmer Optical).
(2) The viscosity was measured by a rotation viscometer (BL Type; Made in Tokyo Keiki Co., Ltd.)

EXAMPLE 6

HES (DS 0.54, intrinsic viscosity 0.30, MW 232000) was treated with 0.0125N—HCl shown in Example 5 by the same manner as Example 1.

The resultant HES solution was clear and showed DS 0.54, intrinsic viscosity 0.101 and turbidity 6.0 ppm. The gel-filtration of this solution was carried out with Sephadex G-200. In this case, column size of 2.5cm x 40cm and flow adapter were used. Elution was ascending method and its speed was 0.2–0.3 ml/min. (0.048–0.061 ml/cm$^2$/min). The volume for the following test was 0.25 ml (2.5mg) and one fraction volume was 3 ml. The determination of saccharide was carried out by the Anthron Method, and its results were shown in FIG. 12.

Figure 12:
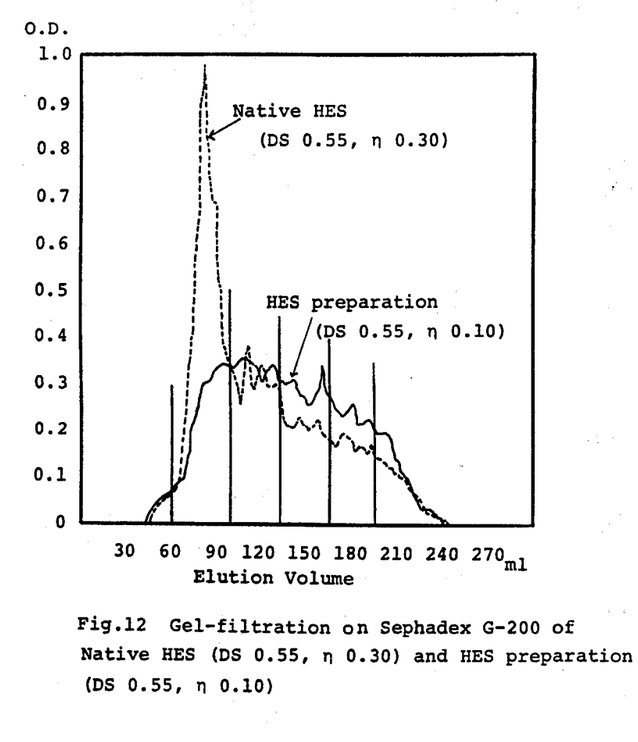
FIG. 12 shows gel-filtration on Sephadex G-200 of Native HES and HES preparation.

That is to say, the part of polymer was broadly shifted to a lower molecular side as much as 40% by the treatment with acid. Moreover, it was concluded from the intrinsic viscosity of hydroxyethyl starch in the last solution that the average molecular weight was about 40,000.

EXAMPLE 7

HES (DS 0.5 – 0.6 preferable 0.55, intrinsic viscosity 0.3) was treated with the same manner as in Examples 1–5. The resultant HES solution possessed a DS 0.55 and intrinsic viscosity of 0.08–0.14 (preferable 0.10). The solution was adjusted to a pH of 6.2 ± 0.5 and was adjusted to 100 ml in total volume with hydroxyethylstarch 6%, NaCl 0.5% (including NaCl which was produced by neutralization), KCl 0.03%, CaCl$_2$.2H$_2$O 0.02%, Na-lactate 0.224% and glucose 1% (W/V%).

This slightly turbid solution was filtered clearly, packed in bottles, and sealed. This HES preparation can be used as the product of plasma substitute by means of sterilizing by heating at 100°C for 1 hour.

What is claimed is:

1. A process for preparing a plasma substitute for injection by treating hydroxyethyl starch having a DS of 0.5–0.6 and an intrinsic viscosity of 0.28–0.30 dl/g in water with dilute hydrochloric acid to obtain a hydroxyethyl starch solution having a DS of 0.5–0.6 and an intrinsic viscosity of 0.08–0.14 dl/g, adding physiologically acceptable electrolytes and glucose to the solution and then diluting the solution with sufficient water to give an isotonic plasma substittute having an oncotic pressure and osmotic pressure equal to those of plasma.

2. The process of claim 1, wherein the hydrochloric acid concentration is 0.01 to 0.03 N and the concentration of hydroxyethyl starch having an intrinsic viscosity of 0.28–0.30 dl/g is 8 to 10 percent.

3. The process of claim 1, wherein the amount of the electrolytes and glucose added produce final concentrations of 0.5% (w/v) of sodium chloride, 0.03% (w/v) of potassium chloride, 0.02% (w/v) of calcium chloride dihydrate, 0.224% (w/v) of sodium lactate and 1% (w/v) of glucose.

4. An isotonic plasma substitute having an oncotic pressure and osmotic pressure equal to those of plasma, consisting of 6% (w/v) hydroxyethyl starch having a DS of 0.5 – 0.6 and an intrinsic viscosity of 0.08–0.14 dl/g, physiologically acceptable electrolytes, glucose and water.

5. An isotonic plasma substitute consisting of 6% (w/v) hydroxyethyl starch having a DS of 0.5 – 0.6 and an intrinsic viscosity of 0.08–0.14 dl/g, 0.5% (w/v) sodium chloride, 0.03% (w/v) potassium chloride, 0.02% (w/v) calcium chloride dihydrate, 0.224% (w/v) sodium lactate and 1% (w/v) glucose, and water.

* * * * *

UNITED STATES PATENT OFFICE
CERTIFICATE OF CORRECTION

Patent No. 3,937,821　　　　　　　　　　Dated February 10, 1976

Inventor(s) Tsutomu Irikura et al

It is certified that error appears in the above-identified patent and that said Letters Patent are hereby corrected as shown below:

In the heading of the Patent [75] should read as follows:

--[75]　　Tsutomu Irikura,　Tokyo;
　　　　　Kazunari Shirai,　Tokyo;
　　　　　Mamoru Tada,　　　Urawa;
　　　　　Terumi Tamada ,　Tokyo;
　　　　　Jun Imai,　　　　Tokyo;
　　　　　Kodo Okada,　　　Tokyo
　　　　　Ryozo Ishida,　　Saitama,
　　　　　all of Japan --.

Signed and Sealed this twentieth Day of April 1976

[SEAL]

Attest:

RUTH C. MASON　　　　　　　　　　C. MARSHALL DANN
Attesting Officer　　　　　　　Commissioner of Patents and Trademarks